US008927739B2

(12) United States Patent  (10) Patent No.:  US 8,927,739 B2
Qiu et al.  (45) Date of Patent:  Jan. 6, 2015

(54) PROCESSES FOR THE PREPARATION OF 5-AZASPIRO[2.4]HEPTANE-6-CARBOXYLIC ACID AND ITS DERIVATIVES

(71) Applicant: Enanta Pharmaceuticals, Inc., Watertown, MA (US)

(72) Inventors: Yao-Ling Qiu, Andover, MA (US); Xiaowen Peng, Cambridge, MA (US); In Jong Kim, Lexington, MA (US); Hui Cao, Belmont, MA (US); Datong Tang, Newton, MA (US); Yat Sun Or, Watertown, MA (US); Guoqiang Wang, Belmont, MA (US); Guoyou Xu, Framingham, MA (US)

(73) Assignee: Enanta Pharmaceuticals, Inc., Watertown, MA (US)

( * ) Notice: Subject to any disclaimer, the term of this patent is extended or adjusted under 35 U.S.C. 154(b) by 0 days.

(21) Appl. No.: 14/082,406

(22) Filed: Nov. 18, 2013

(65) Prior Publication Data
US 2014/0187793 A1 Jul. 3, 2014

Related U.S. Application Data

(63) Continuation of application No. PCT/US2012/038240, filed on May 17, 2012.

(60) Provisional application No. 61/487,436, filed on May 18, 2011.

(51) Int. Cl.
C07D 209/54 (2006.01)

(52) U.S. Cl.
CPC .................................... *C07D 209/54* (2013.01)
USPC ........................................................ 548/408

(58) Field of Classification Search
None
See application file for complete search history.

(56) References Cited

U.S. PATENT DOCUMENTS

| | | | |
|---|---|---|---|
| 3,328,391 A | 6/1967 | Sandri et al. |
| 3,363,012 A | 1/1968 | Norell |
| 5,286,723 A | 2/1994 | Hayakawa et al. |
| 5,545,779 A | 8/1996 | Pies et al. |
| 5,631,385 A | 5/1997 | Drauz et al. |
| 5,935,982 A | 8/1999 | Dykstra et al. |
| 6,469,023 B1 | 10/2002 | Takemura et al. |
| 6,579,976 B2 | 6/2003 | Takamatsu et al. |
| 7,141,574 B2 | 11/2006 | Beaulieu et al. |
| 7,563,805 B2 | 7/2009 | Takemura et al. |
| 8,188,132 B2 | 5/2012 | Or et al. |
| 8,242,156 B2 | 8/2012 | Qiu et al. |
| 8,314,135 B2 | 11/2012 | Qiu et al. |
| 8,420,686 B2 | 4/2013 | Or et al. |
| 8,426,458 B2 | 4/2013 | Or et al. |
| 2005/0222198 A1 | 10/2005 | Bondy et al. |
| 2006/0003942 A1 | 1/2006 | Tung et al. |
| 2006/0058317 A1 | 3/2006 | Gravestock et al. |
| 2006/0178399 A1 | 8/2006 | Nishizawa et al. |
| 2007/0197558 A1 | 8/2007 | Betebenner et al. |
| 2007/0244148 A1 | 10/2007 | Bondy et al. |
| 2007/0299068 A1 | 12/2007 | Karp et al. |
| 2008/0044379 A1 | 2/2008 | Bachand et al. |
| 2008/0194803 A1 | 8/2008 | Sinclair et al. |
| 2008/0299075 A1 | 12/2008 | Bachand et al. |
| 2009/0004140 A1 | 1/2009 | Qiu et al. |
| 2009/0020478 A1 | 1/2009 | Erwe et al. |
| 2009/0047247 A1 | 2/2009 | Qiu et al. |

(Continued)

FOREIGN PATENT DOCUMENTS

| | | |
|---|---|---|
| WO | 2005085242 A1 | 9/2005 |
| WO | 2006133326 A1 | 12/2006 |

(Continued)

OTHER PUBLICATIONS

Kondrashov, et al., "Reactions of N-(Polychloroethylidene)arene- and-trifluoromethanesulfonamides with Indoles," Russian Journal of Organic Chemistry, 44(1):86-94, 2008.

(Continued)

*Primary Examiner* — Michael Barker
(74) *Attorney, Agent, or Firm* — Roy P. Issac; Carolyn S. Elmore, Esq.; Elmore Patent Law Group, P.C.

(57) ABSTRACT

The present invention relates generally to an improved process for the preparation of 5-azaspiro[2.4]heptane-6-carboxylic acid and its derivatives which are useful intermediates in the synthesis of biologically active molecules, especially in the synthesis of hepatits C virus NS5A inhibitors. In particular, the present invention relates to processes and intermediates for the preparation of compounds of formulae (Ia), (Ib) and (Ic):

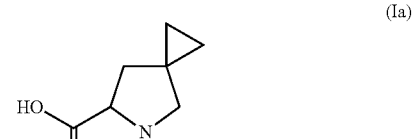

(Ia)

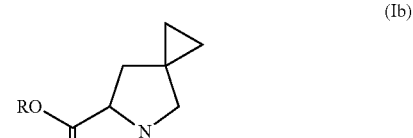

(Ib)

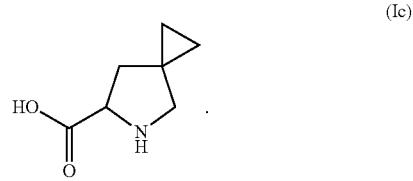

(Ic)

11 Claims, No Drawings

(56) References Cited

U.S. PATENT DOCUMENTS

| | | |
|---|---|---|
| 2009/0202478 A1 | 8/2009 | Bachand et al. |
| 2009/0202483 A1 | 8/2009 | Bachand et al. |
| 2009/0317360 A1 | 12/2009 | Rai et al. |
| 2010/0226883 A1 | 9/2010 | Qiu et al. |
| 2010/0233120 A1 | 9/2010 | Bachand et al. |
| 2010/0233122 A1 | 9/2010 | Qiu et al. |
| 2010/0260708 A1 | 10/2010 | Belema et al. |
| 2010/0260715 A1 | 10/2010 | Or et al. |
| 2010/0305117 A1 | 12/2010 | Herdewijn et al. |
| 2010/0310512 A1 | 12/2010 | Guo et al. |
| 2010/0316607 A1 | 12/2010 | Or et al. |
| 2011/0008288 A1 | 1/2011 | Or et al. |
| 2011/0064695 A1 | 3/2011 | Qiu et al. |
| 2011/0064696 A1 | 3/2011 | Or et al. |
| 2011/0064697 A1 | 3/2011 | Qiu et al. |
| 2011/0064698 A1 | 3/2011 | Or et al. |
| 2011/0070196 A1 | 3/2011 | Qiu et al. |
| 2011/0070197 A1 | 3/2011 | Or et al. |
| 2011/0142798 A1 | 6/2011 | Qiu et al. |
| 2011/0189129 A1 | 8/2011 | Qiu et al. |
| 2011/0195044 A1 | 8/2011 | Romine |
| 2011/0217261 A1 | 9/2011 | Or et al. |
| 2011/0250172 A1 | 10/2011 | Qiu et al. |
| 2011/0300104 A1 | 12/2011 | Qiu et al. |
| 2012/0039848 A1 | 2/2012 | Qiu et al. |
| 2012/0095211 A1 | 4/2012 | Buckman et al. |

FOREIGN PATENT DOCUMENTS

| | | |
|---|---|---|
| WO | 2007128086 A2 | 11/2007 |
| WO | 2008021927 A2 | 2/2008 |
| WO | 2008021928 A2 | 2/2008 |
| WO | 2008021936 A2 | 2/2008 |
| WO | 2008106139 A1 | 9/2008 |
| WO | 2008144380 A1 | 11/2008 |
| WO | 2009020825 A1 | 2/2009 |
| WO | 2009020828 A1 | 2/2009 |
| WO | 2009102318 A1 | 8/2009 |
| WO | 2009102325 A1 | 8/2009 |
| WO | 2009102568 A1 | 8/2009 |
| WO | 2009102633 A1 | 8/2009 |
| WO | 2009102694 A1 | 8/2009 |
| WO | 2010014744 A1 | 2/2010 |
| WO | 2010017401 A1 | 2/2010 |
| WO | 2010039793 A1 | 4/2010 |
| WO | 2010065668 A1 | 6/2010 |
| WO | 2010065674 A1 | 6/2010 |
| WO | 2010065681 A1 | 6/2010 |
| WO | 2010096302 A1 | 8/2010 |
| WO | 2010096777 A1 | 8/2010 |
| WO | 2010099527 A1 | 9/2010 |
| WO | 2010111483 A1 | 9/2010 |
| WO | 2010111534 A1 | 9/2010 |
| WO | 2010111673 A1 | 9/2010 |
| WO | 2010117635 A1 | 10/2010 |
| WO | 2010117704 A1 | 10/2010 |
| WO | 2010117977 A1 | 10/2010 |
| WO | 2010120621 A1 | 10/2010 |
| WO | 2010120935 A1 | 10/2010 |
| WO | 2010122162 A1 | 10/2010 |
| WO | 2010132538 A1 | 11/2010 |
| WO | 2010132810 A1 | 11/2010 |
| WO | 2010138368 A1 | 12/2010 |
| WO | 2010138488 A1 | 12/2010 |
| WO | 2010138790 A1 | 12/2010 |
| WO | 2010138791 A1 | 12/2010 |
| WO | 2010144646 A2 | 12/2010 |
| WO | 2011004276 A1 | 1/2011 |
| WO | 2011009084 A2 | 1/2011 |
| WO | 2011015657 A1 | 2/2011 |
| WO | 2011015658 A1 | 2/2011 |
| WO | 2011026920 A1 | 3/2011 |
| WO | 2011028596 A1 | 3/2011 |
| WO | 2011031904 A1 | 3/2011 |
| WO | 2011031934 A1 | 3/2011 |
| WO | 2011050146 A1 | 4/2011 |
| WO | 2011150243 A1 | 12/2011 |
| WO | 2012018325 A1 | 2/2012 |

OTHER PUBLICATIONS

Porter, W. H., "Resolution of chiral drugs," Pure & Appl Chem, 63(8): 1119-1122 (1991).

Bressanelli, et al., "Crystal Structure of the RNA-dependent RNA Polymerase of Hepatitis C Virus," PNAS, 96 (23):13034-13039, 1999.

International Search Report for PCT/US2010/24447, dated Apr. 12, 2010.

Tellinghuisen, et al., "Structure of the zinc-binding domain of an essential component of the hepatitis C virus replicase," Nature letters, 435:374-479 & 374, abstract (2005).

"Interferon", http://en.wiktionary.org/wiki/interferon, accessed Apr. 6, 2011.

"Inhibitor", http://www.biology-online.org/dictionary/Inhibitor, accessed Apr. 6, 2011.

International Search Report for PCT/US12/57834 dated Nov. 5, 2012.

Taschner, et al., "Sodium Trichloroacetate," E-Eros Encyclopedia of Reagents for Organic Synthesis, Wiley, pp. 8981-8983, 2001.

Chatgilialoglu, et al., "Tris(trimethylsilyl)silane. A New Reducing Agent," The Journal of Organic Chemistry, 53 (15):3641-3642, 1988.

Wei, et al,. "Design, synthesis and antibacterial activity of 3-methylenepyrrolidine formyl hydroxyamino derivatives as novel peptide deformylase inhibitors," Bioorganic & Medicinal Chemistry Letters, 21:1060-1063, 2011.

Lung, et al., "Reaction of Some Monoterpenes with Dichlorocarbene," Journal of Sun Yat-sen University, 2:206-216, 1965. (English Abstract attached).

PROCESSES FOR THE PREPARATION OF 5-AZASPIRO[2.4]HEPTANE-6-CARBOXYLIC ACID AND ITS DERIVATIVES

RELATED APPLICATIONS

This application is a continuation of International Application No. PCT/US2012/038240, which designated the United States and was filed on May 17, 2012, published in English, which claims the benefit of U.S. Provisional Application No. 61/487,436, filed on May 18, 2011. The entire teaching of the above applications is incorporated herein by reference.

TECHNICAL FIELD

The present invention relates generally to an improved process for the preparation of 5-azaspiro[2.4]heptane-6-carboxylic acid and its derivatives which are useful intermediates in the synthesis of biologically active molecules, especially in the synthesis of hepatits C virus NS5A inhibitors.

BACKGROUND OF THE INVENTION 5-azaspiro[2.4]heptane-6-carboxylic acid, or 4-spirocyclopropyl proline, and its derivatives have been found to be useful intermediates in the preparation of reagents for the treatment of HCV infection (for example, see: WO2009/102325A1, WO2010/099527A1 and WO2010/132601A1). The preparation of 4-spirocyclopropyl proline derivatives generally involves treatment of a 4-exocyclic methylene-substituted proline compound with a metal carbenoid generated through Simmon-Smith reaction or its different variations (e.g. $Et_2Zn/ClCH_2I$, $Et_2Zn/CH_2I_2/CF_3COOH$). The reaction suffers from incomplete conversion and hence low yield and difficult purification. It also frequently requires the use of excess amount of extremely air-sensitive and hightly flammable reagent, $Et_2Zn$, which is difficult to handle and poses a great fire harzard. These current processes are not amenable to large scale synthesis. There is an urgent need for the development of a practical synthetic process for the preparation of 4-spirocyclopropyl proline derivatives.

SUMMARY OF THE INVENTION

The present invention provides methods for preparing compounds of Formula (I):

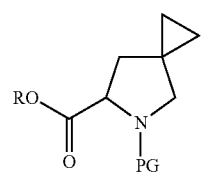

(I)

wherein R is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably, R is hydrogen, optionally substituted $C_1$-$C_4$ alkyl or optionally substituted aryl; more preferably, R is hydrogen, methyl, benzyl, tert-butyl or phenyl; and PG is selected from the group consisting of —R, —C(O)—R, —C(O)—OR, —S(O)$_2$—R, —C(O)NR$_2$, and —S(O)$_2$NR$_2$; preferably, PG is hydrogen or —C(O)—OR.

A preferred embodiment of a compound of Formula (I) is the compound of Formula (Ia):

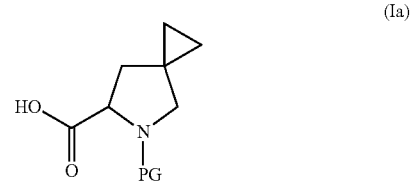

(Ia)

wherein PG is as previously defined.

Another preferred embodiment of a compound of Formula (I) is the compound of Formula (Ib):

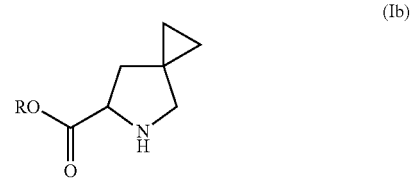

(Ib)

wherein R is as previously defined.

Another preferred embodiment of a compound of Formula (I) is the compound of Formula (Ic):

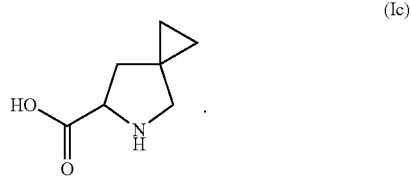

(Ic)

The invention related to the preparation of a spiropropane compound of Formula (I, Ia, Ib or Ic), through addition of a dihalocarbene to an exocyclic olefinic double bond to give a dihalogenated cyclopropane intermediate, followed by reductive hydrodehalogenation.

The invention further relates to methods for increasing product yield and decreasing process steps for intermediate and large scale production of compounds of Formula (Ia) and particularly, (S)-5-(tert-butoxycarbonyl)-5-azaspiro[2.4]heptane-6-carboxylic acid. These compounds are useful as reagents in the synthesis of HCV inhibitors, especially those that have been disclosed in WO2010/099527A1.

DETAILED DESCRIPTION OF THE INVENTION

In its principal embodiment, the present invention provides a process for the preparation of compounds of Formula (I):

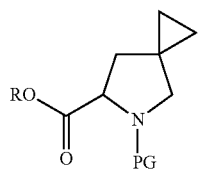

(I)

wherein R is selected from the group consisting of hydrogen, $C_1$-$C_8$ alkyl, $C_2$-$C_8$ alkenyl, $C_2$-$C_8$ alkynyl, $C_3$-$C_8$ cycloalkyl, $C_3$-$C_8$ cycloalkenyl, heterocyclic, aryl, and heteroaryl, each optionally substituted; preferably, R is hydrogen, optionally substituted $C_1$-$C_4$ alkyl or optionally substituted aryl; more preferably, R is hydrogen, methyl, benzyl, tert-butyl or phenyl; and PG is selected from the group consisting of —R, —C(O)—R, —C(O)—OR, —S(O)$_2$—R, —C(O)NR$_2$, and —S(O)$_2$NR$_2$; preferably, PG is hydrogen or —C(O)—OR;

the process comprising:

(a) reacting a compound of Formula (II):

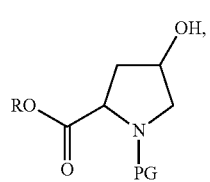

(II)

wherein R and PG are as previously defined;
with an oxidizing reagent to yield a compound of Formula (III):

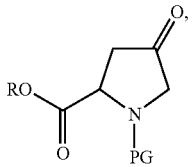

(III)

wherein R and PG are as previously defined;
(b) treating the compound of Formula (III) with an olefination reagent to provide a compound of Formula (IV):

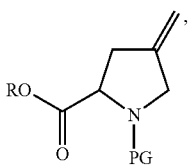

(IV)

wherein R and PG are as previously defined;
(c) reacting the compound of Formula (IV) with a monohalocarbene or a dihalocarbene, preferably generated from a thermal decomposition of a trihaloacetate salt, optionally in the presence of a halide salt or a phase-transfer catalyst to yield compounds of Formula (V):

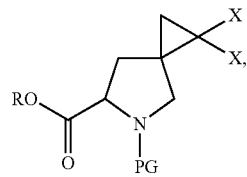

(V)

wherein R and PG are as previously defined; X at each occurrence is independently selected from the group consisting of hydrogen, bromine and chlorine; wherein at least one of the two X groups is chlorine or bromine;
(d) maintaining the compound of Formula (V) under conditions for reductive hydrodehalogenation to provide a compound of Formula (I):

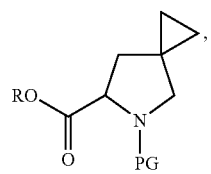

(I)

wherein R and PG are as previously defined; and
(e) optionally, (i) hydrolyzing the compound of Formula (I) to yield a compound of Formula (Ia);
(ii) deprotecting the compound of Formula (I) to yield the compound of Formula (Ib); or
(iii) hydrolyzing and deprotecting the compound of Formula (I) to yield the compound of Formula (Ic):

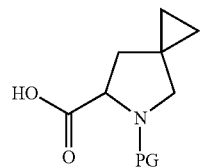

(Ia)

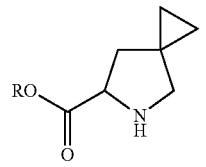

(Ib)

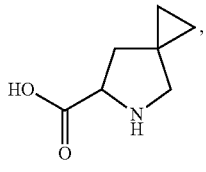

(Ic)

wherein PG or R is as previously defined.

In one embodiment of the compounds of Formulae (I-V and Ib), R is hydrogen, optionally substituted $C_1$-$C_4$ alkyl or optionally substituted aryl; in yet another embodiment, R is hydrogen, methyl, benzyl, tert-butyl or phenyl.

In another embodiment of the compounds of Formulae (I-V and Ia), PG is —C(O)—OR, wherein R is as previously defined; in yet another embodiment, PG is Boc or Cbz.

In still another embodiment of the compounds of Formula (V), X at each occurrence is independently hydrogen or bromine and at least one of the two X groups is bromine.

In still another embodiment the dihalocarbene of step (c) is generated by thermal decomposition of a trihaloacetate salt, optionally in the presence of a halide or phase-transfer catalyst.

In an embodiment, the trihaloacetate salt is sodium trichloroacetate or sodium tribromoacetate. In still another embodiment, step (c) is conducted in the presence of a halide salt or a phase-transfer catalyst. In an embodiment, the halide salt is also a phase-transfer catalyst, such as a quaternary ammonium halide salt or a phosphonium halide salt.

In still another embodiment step (d) comprises reacting the compound of Formula (V) with a reductive radical reagent or a single-electron reagent.

In an embodiment, step (d) comprises reacting the compound of Formula (V) with a reductive radical reagent in the presence of a radical initiator. In one embodiment, the reductive radical reagent is a stannane, a silane, a sulfide, or a low-valent phosphorous compound. In still another embodiment, the reductive radical reagent is tris(trimethylsilyl)silane or hypophosphorous acid ($H_3PO_2$).

In still another embodiment, step (d) comprises reacting the compound of Formula (V) with a single electron transfer reagent. In an embodiment, the single electron transfer reagent is a low-valent metallic reagent. In still another embodiment, the single electron transfer reagent used in step (d) is elemental Zn or Mg.

DEFINITIONS

Listed below are definitions of various terms used to describe this invention. These definitions apply to the terms as they are used throughout this specification and claims, unless otherwise limited in specific instances, either individually or as part of a larger group.

The term "aryl," as used herein, refers to a mono- or polycyclic carbocyclic ring system comprising at least one aromatic ring, including, but not limited to, phenyl, naphthyl, tetrahydronaphthyl, indanyl, idenyl. A polycyclic aryl is a polycyclic ring system that comprises at least one aromatic ring. Polycyclic aryls can comprise fused rings, covalently attached rings or a combination thereof.

The term "heteroaryl," as used herein, refers to a mono- or polycyclic aromatic radical having one or more ring atom selected from S, O and N; and the remaining ring atoms are carbon, wherein any N or S contained within the ring may be optionally oxidized. Heteroaryl includes, but is not limited to, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl. A polycyclic heteroaryl can comprise fused rings, covalently attached rings or a combination thereof.

In accordance with the invention, aromatic groups can be substituted or unsubstituted.

The terms "$C_1$-$C_4$ alkyl," "$C_1$-$C_6$ alkyl," or "$C_1$-$C_8$ alkyl," as used herein, refer to saturated, straight- or branched-chain hydrocarbon radicals containing between one and four, one and six, one and eight carbon atoms, respectively. Examples of $C_1$-$C_8$ alkyl radicals include, but are not limited to, methyl, ethyl, propyl, isopropyl, n-butyl, tert-butyl, neopentyl, n-hexyl, heptyl and octyl radicals.

The terms "$C_2$-$C_8$ alkenyl," or "$C_2$-$C_4$ alkenyl," as used herein, refer to straight- or branched-chain hydrocarbon radicals containing from two to eight, or two to four carbon atoms, having at least one carbon-carbon double bond by the removal of a single hydrogen atom. Alkenyl groups include, but are not limited to, for example, ethenyl, propenyl, butenyl, 1-methyl-2-buten-1-yl, heptenyl, octenyl, and the like.

The terms "$C_2$-$C_8$ alkynyl," or "$C_2$-$C_4$ alkynyl," as used herein, refer to straight- or branched-chain hydrocarbon radicals containing from two to eight, or two to four carbon atoms, having at least one carbon-carbon triple bond by the removal of a single hydrogen atom. Representative alkynyl groups include, but are not limited to, for example, ethynyl, 1-propynyl, 1-butynyl, heptynyl, octynyl, and the like.

The term "$C_3$-$C_8$ cycloalkyl," as used herein, refers to a monocyclic or polycyclic saturated carbocyclic ring compound, and the carbon atoms may be optionally oxo-substituted. Examples of $C_3$-$C_8$ cycloalkyl include, but not limited to, cyclopropyl, cyclobutyl, cyclopentyl, cyclohexyl, cyclopentyl and cyclooctyl; and examples of $C_4$-$C_7$ cycloalkyl include, but not limited to, cyclopentyl, cyclohexyl, bicyclo[2.2.1]heptyl, and the like.

The term "$C_3$-$C_8$ cycloalkenyl", as used herein, refers to monocyclic or polycyclic carbocyclic ring compound having at least one carbon-carbon double bond and the carbon atoms may be optionally oxo-substituted. Examples of $C_3$-$C_8$ cycloalkenyl include, but not limited to, cyclopropenyl, cyclobutenyl, cyclopentenyl, cyclohexenyl, cycloheptenyl, cyclooctenyl, and the like; and examples of $C_5$-$C_7$ cycloalkenyl include, but not limited to, cyclopentenyl, cyclohexenyl, cycloheptenyl, and the like.

It is understood that any alkyl, alkenyl, alkynyl, cycloalkyl, heterocyclic and cycloalkenyl moiety described herein can also be an aliphatic group or an alicyclic group.

An "aliphatic" group is a non-aromatic moiety comprised of any combination of carbon atoms, hydrogen atoms, halogen atoms, oxygen, nitrogen or other atoms, and optionally contains one or more units of unsaturation, e.g., double and/or triple bonds.

Examples of aliphatic groups are functional groups, such as, O, OH, NH, $NH_2$, C(O), $S(O)_2$, C(O)O, C(O)NH, OC(O)O, OC(O)NH, $OC(O)NH_2$, $S(O)_2NH$, $S(O)_2NH_2$, NHC(O)$NH_2$, NHC(O)C(O)NH, $NHS(O)_2NH$, $NHS(O)_2NH_2$, $C(O)NHS(O)_2$, $C(O)NHS(O)_2NH$ or $C(O)NHS(O)_2NH_2$, and the like, groups comprising one or more functional groups, non-aromatic hydrocarbons (optionally substituted), and groups wherein one or more carbons of a non-aromatic hydrocarbon (optionally substituted) is replaced by a functional group. Carbon atoms of an aliphatic group can be optionally oxo-substituted. An aliphatic group may be straight chained, branched, cyclic, or a combination thereof and preferably contains between about 1 and about 24 carbon atoms, more typically between about 1 and about 12 carbon atoms. In addition to aliphatic hydrocarbon groups, as used herein, aliphatic groups expressly include, for example, alkoxyalkyls, polyalkoxyalkyls, such as polyalkylene glycols, polyamines, and polyimines, for example. Aliphatic groups may be optionally substituted. A linear aliphatic group is a non-cyclic aliphatic group. It is to be understood that when an aliphatic group or a linear aliphatic group is said to "contain" or "include" or "comprise" one or more specified functional groups, the linear aliphatic group can be selected from one or more of the specified functional groups or a combination thereof, or a group wherein one or more carbons of a non-aromatic hydrocarbon (optionally substituted) is replaced by a specified functional group. In another aspect of the invention, an exemplary linear aliphatic group is an alkyl, alkenyl or alkynyl, each optionally substituted, which is interrupted or terminated by a functional group such as described herein.

The term "alicyclic," as used herein, denotes a monovalent group derived from a monocyclic or bicyclic saturated carbocyclic ring compound by the removal of a single hydrogen atom, and the carbon atoms may be optionally oxo-substituted. Examples include, but not limited to, cyclopropyl, cyclobutyl, cyclopentyl, cyclohexyl, bicyclo[2.2.1]heptyl, and bicyclo[2.2.2]octyl. Such alicyclic groups may be further substituted.

The terms "heterocyclic" or "heterocycloalkyl" can be used interchangeably and referred to a non-aromatic ring or a bi- or tri-cyclic group fused system, where (i) each ring system contains at least one heteroatom independently selected from oxygen, sulfur and nitrogen, (ii) each ring system can be saturated or unsaturated (iii) the nitrogen and sulfur heteroatoms may optionally be oxidized, (iv) the nitrogen heteroatom may optionally be quaternized, (v) any of the above rings may be fused to an aromatic ring, and (vi) the remaining ring atoms are carbon atoms which may be optionally oxo-substituted. Representative heterocycloalkyl groups include, but are not limited to, 1,3-dioxolane, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, quinoxalinyl, pyridazinonyl, and tetrahydrofuryl. Such heterocyclic groups may be further substituted. Heteroaryl or heterocyclic groups can be C-attached or N-attached (where possible).

It is understood that any alkyl, alkenyl, alkynyl, alicyclic, cycloalkyl, cycloalkenyl, aryl, heteroaryl, heterocyclic, aliphatic moiety or the like, described herein can also be a divalent or multivalent group when used as a linkage to connect two or more groups or substituents, which can be at the same or different atom(s).

The term "substituted" refers to substitution by independent replacement of one, two, or three or more of the hydrogen atoms with substituents including, but not limited to, —F, —Cl, —Br, —I, —OH, protected hydroxy, —$NO_2$, —$N_3$, —CN, —$NH_2$, protected amino, oxo, thioxo, —NH—$C_1$-$C_{12}$-alkyl, —NH—$C_2$-$C_8$-alkenyl, —NH—$C_2$-$C_8$-alkynyl, —NH—$C_3$-$C_{12}$-cycloalkyl, —NH-aryl, —NH-heteroaryl, —NH-heterocycloalkyl, -dialkylamino, -diarylamino, -diheteroarylamino, —O—$C_1$-$C_{12}$-alkyl, —O—$C_2$-$C_8$-alkenyl, —O—$C_2$-$C_8$-alkynyl, —O—$C_3$-$C_{12}$-cycloalkyl, —O-aryl, —O-heteroaryl, —O-heterocycloalkyl, —C(O)—$C_1$-$C_{12}$-alkyl, —C(O)—$C_2$-$C_8$-alkenyl, —C(O)—$C_2$-$C_8$-alkynyl, —C(O)—$C_3$-$C_{12}$-cycloalkyl, —C(O)-aryl, —C(O)-heteroaryl, —C(O)-heterocycloalkyl, —$CONH_2$, —CONH—$C_1$-$C_{12}$-alkyl, —CONH—$C_2$-$C_8$-alkenyl, —CONH—$C_2$-$C_8$-alkynyl, —CONH—$C_3$-$C_{12}$-cycloalkyl, —CONH-aryl, —CONH-heteroaryl, —CONH-heterocycloalkyl, —$OCO_2$—$C_1$-$C_{12}$-alkyl, —$OCO_2$—$C_2$-$C_8$-alkenyl, —$OCO_2$—$C_2$-$C_8$-alkynyl, —$OCO_2$—$C_3$-$C_{12}$-cycloalkyl, —$OCO_2$-aryl, —$OCO_2$-heteroaryl, —$OCO_2$-heterocycloalkyl, —$CO_2$—$C_1$-$C_{12}$ alkyl, —$CO_2$—$C_2$-$C_8$ alkenyl, —$CO_2$—$C_2$-$C_8$ alkynyl, $CO_2$—$C_3$-$C_{12}$-cycloalkyl, —$CO_2$-aryl, $CO_2$-heteroaryl, $CO_2$-heterocycloalkyl, —$OCONH_2$, —OCONH—$C_1$-$C_{12}$-alkyl, —OCONH—$C_2$-$C_8$-alkenyl, —OCONH—$C_2$-$C_8$-alkynyl, —OCONH—$C_3$-$C_{12}$-cycloalkyl, —OCONH-aryl, —OCONH-heteroaryl, —OCONH-heterocyclo-alkyl, —NHC(O)H, —NHC(O)—$C_1$-$C_{12}$-alkyl, —NHC(O)—$C_2$-$C_8$-alkenyl, —NHC(O)—$C_2$-$C_8$-alkynyl, —NHC(O)—$C_3$-$C_{12}$-cycloalkyl, —NHC(O)-aryl, —NHC(O)-heteroaryl, —NHC(O)-heterocycloalkyl, —$NHCO_2$—$C_1$-$C_{12}$-alkyl, —$NHCO_2$—$C_2$-$C_8$-alkenyl, —$NHCO_2$—$C_2$-$C_8$-alkynyl, —$NHCO_2$—$C_3$-$C_{12}$-cycloalkyl, —$NHCO_2$-aryl, —$NHCO_2$-heteroaryl, —$NHCO_2$-heterocycloalkyl, —$NHC(O)NH_2$, —NHC(O)NH—$C_1$-$C_{12}$-alkyl, —NHC(O)NH—$C_2$-$C_8$-alkenyl, —NHC(O)NH—$C_2$-$C_8$-alkynyl, —NHC(O)NH—$C_3$-$C_{12}$-cycloalkyl, —NHC(O)NH-aryl, —NHC(O)NH-heteroaryl, —NHC(O)NH-heterocycloalkyl, NHC(S)$NH_2$, —NHC(S)NH—$C_1$-$C_{12}$-alkyl, —NHC(S)NH—$C_2$-$C_8$-alkenyl, —NHC(S)NH—$C_2$-$C_8$-alkynyl, —NHC(S)NH—$C_3$-$C_{12}$-cycloalkyl, —NHC(S)NH-aryl, —NHC(S)NH-heteroaryl, —NHC(S)NH-heterocycloalkyl, —$NHC(NH)NH_2$, —NHC(NH)NH—$C_1$-$C_{12}$-alkyl, —NHC(NH)NH—$C_2$-$C_8$-alkenyl, —NHC(NH)NH—$C_2$-$C_8$-alkynyl, —NHC(NH)NH—$C_3$-$C_{12}$-cycloalkyl, —NHC(NH)NH-aryl, —NHC(NH)NH-heteroaryl, —NHC(NH)NH-heterocycloalkyl, —NHC(NH)—$C_1$-$C_{12}$-alkyl, —NHC(NH)—$C_2$-$C_8$-alkenyl, —NHC(NH)—$C_2$-$C_8$-alkynyl, —NHC(NH)—$C_3$-$C_{12}$-cycloalkyl, —NHC(NH)-aryl, —NHC(NH)-heteroaryl, —NHC(NH)-heterocycloalkyl, —C(NH)NH—$C_1$-$C_{12}$-alkyl, —C(NH)NH—$C_2$-$C_8$-alkenyl, —C(NH)NH—$C_2$-$C_8$-alkynyl, —C(NH)NH—$C_3$-$C_{12}$-cycloalkyl, —C(NH)NH-aryl, —C(NH)NH-heteroaryl, —C(NH)NH-heterocycloalkyl, —S(O)—$C_1$-$C_{12}$-alkyl, —S(O)—$C_2$-$C_8$-alkenyl, —S(O)—$C_2$-$C_8$-alkynyl, —S(O)—$C_3$-$C_{12}$-cycloalkyl, —S(O)-aryl, —S(O)-heteroaryl, —S(O)-heterocycloalkyl, —$SO_2NH_2$, —$SO_2NH$—$C_1$-$C_{12}$-alkyl, —$SO_2NH$—$C_2$-$C_8$-alkenyl, —$SO_2NH$—$C_2$-$C_8$-alkynyl, —$SO_2NH$—$C_3$-$C_{12}$-cycloalkyl, —$SO_2NH$-aryl, —$SO_2NH$-heteroaryl, —$SO_2NH$-heterocycloalkyl, —$NHSO_2$—$C_1$-$C_{12}$-alkyl, —$NHSO_2$—$C_2$-$C_8$-alkenyl, —$NHSO_2$—$C_2$-$C_8$-alkynyl, —$NHSO_2$—$C_3$-$C_{12}$-cycloalkyl, —$NHSO_2$-aryl, —$NHSO_2$-heteroaryl, —$NHSO_2$-heterocycloalkyl, —$CH_2NH_2$, —$CH_2SO_2CH_3$, -aryl, -arylalkyl, -heteroaryl, -heteroarylalkyl, -heterocycloalkyl, —$C_3$-$C_{12}$-cycloalkyl, polyalkoxyalkyl, polyalkoxy, -methoxymethoxy, -methoxyethoxy, —SH, —S—$C_1$-$C_{12}$-alkyl, —S—$C_2$-$C_8$-alkenyl, —S—$C_2$-$C_8$-alkynyl, —S—$C_3$-$C_{12}$-cycloalkyl, —S-aryl, —S-heteroaryl, —S-heterocycloalkyl, or methylthio-methyl. It is understood that the aryls, heteroaryls, alkyls, and the like can be further substituted.

The term "halogen," as used herein, refers to an atom selected from fluorine, chlorine, bromine and iodine.

The term "hydrogen" includes hydrogen and deuterium. In addition, the recitation of an atom includes other isotopes of that atom so long as the resulting compound is pharmaceutically acceptable.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein.

The synthesized compounds can be separated from a reaction mixture and further purified by a method such as column chromatography, high pressure liquid chromatography, or recrystallization. As can be appreciated by the skilled artisan, further methods of synthesizing the compounds of the formulae herein will be evident to those of ordinary skill in the art. Additionally, the various synthetic steps may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995).

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

The compounds described herein contain one or more asymmetric centers and thus give rise to enantiomers, diastereomers, and other stereoisomeric forms that may be defined, in terms of absolute stereochemistry, as (R)- or (S)-, or as (D)- or (L)- for amino acids. The present invention is meant to include all such possible isomers, as well as their racemic and optically pure forms. Optical isomers may be prepared from their respective optically active precursors by the procedures described above, or by resolving the racemic mixtures. The resolution can be carried out in the presence of a resolving agent, by chromatography or by repeated crystallization or by some combination of these techniques which are known to those skilled in the art. Further details regarding resolutions can be found in Jacques, et al., *Enantiomers, Racemates, and Resolutions* (John Wiley & Sons, 1981). When the compounds described herein contain olefinic double bonds, other unsaturation, or other centers of geometric asymmetry, and unless specified otherwise, it is intended that the compounds include both E and Z geometric isomers or cis- and trans-isomers. Likewise, all tautomeric forms are also intended to be included. The configuration of any carbon-carbon double bond appearing herein is selected for convenience only and is not intended to designate a particular configuration unless the text so states; thus a carbon-carbon double bond or carbon-heteroatom double bond depicted arbitrarily herein as trans may be cis, trans, or a mixture of the two in any proportion.

Suitable concentrations of reactants used in the synthesis processes of the invention are 0.01M to 10M, typically 0.1M to 1M. Suitable temperatures include −10° C. to 250° C., typically −78° C. to 150° C., more typically −78° C. to 100° C., still more typically 0° C. to 100° C. Reaction vessels are preferably made of any material which does not substantial interfere with the reaction. Examples include glass, plastic, and metal. The pressure of the reaction can advantageously be operated at atmospheric pressure. The atmospheres include, for example, air, for oxygen and water insensitive reactions, or nitrogen or argon, for oxygen or water sensitive reactions.

The term "in situ," as used herein, refers to use of an intermediate in the solvent or solvents in which the intermediate was prepared without removal of the solvent.

Unless otherwise defined, all technical and scientific terms used herein are accorded the meaning commonly known to one with ordinary skill in the art. All publications, patents, published patent applications, and other references mentioned herein are hereby incorporated by reference in their entirety.

ABBREVIATIONS

Abbreviations which may be used in the descriptions of the scheme and the examples that follow are: Ac for acetyl; AcOH for acetic acid; AIBN for azobisisobutyronitrile; $Boc_2O$ for di-tert-butyl-dicarbonate; Boc for t-butoxycarbonyl; BPO for benzoyl peroxide; Bz for benzoyl; Bn for benzyl; t-BuOK for potassium tert-butoxide; $Bu_3SnH$ for tributyltin hydride; BOP for (benzotriazol-1-yloxy)tris(dimethylamino)phosphonium Hexafluorophosphate; $Br_3CCO_2Na$ for sodium tribromoacetate; Brine for sodium chloride solution in water; n-BuLi for n-butyl lithium; i-BuLi for i-butyl lithium; t-BuLi for t-butyl lithium; t-BuOH for tert-butanol; $Bu_4NBr$ for tetrabutylammonium bromide; $Bu_4NCl$ for tetrabutylammonium chloride; $Bu_4NI$ for tetrabutylammonium iodide; Cbz for carbobenzyloxy; CDI for carbonyldiimidazole; $CH_2Cl_2$ for dichloromethane; $ClCH_2I$ for chloroiodomethane; $CH_2I_2$ for diiodomethane; $CH_3$ for methyl; $CH_3CN$ for acetonitrile; $Cl_3CCO_2Na$ for sodium trichloroacetate; $Cs_2CO_3$ for cesium carbonate; CuCl for copper (I) chloride; CuI for copper (I) iodide; DBU for 1,8-diazabicyclo[5.4.0]undec-7-ene; DCC for N,N'-dicyclohexylcarbodiimide; DCE for 1,2-dichloroethane; DIBAL-H for diisobutylaluminium hydride; DIPEA or $(i-Pr)_2EtN$ for N,N-diisopropylethyl amine; Dess-Martin periodinane for 1,1,1-tris(acetyloxy)-1,1-dihydro-1,2-benziodoxol-3-(1H)-one; DMAP for 4-dimethylamino-pyridine; DME for 1,2-dimethoxyethane; DMF for N,N-dimethylformamide; DMSO for dimethyl sulfoxide; EDC for N-(3-dimethylaminopropyl)-N'-ethylcarbodiimide; EDC.HCl for N-(3-dimethylamino-propyl)-N'-ethylcarbodiimide hydrochloride; $Et_2Zn$ for diethylzinc; $Et_3BnNBr$ for benzyltriethylammonium bromide; EtOAc for ethyl acetate; EtOH for ethanol; $Et_2O$ for diethyl ether; $Et_2Zn$ for diethyl zinc; Fmoc for 9-fluorenylmethoxycarbonyl; HATU for O-(7-azabenzotriazol-1-yl)-N,N,N',N'-tetramethyluronium hexafluorophosphate; HCl for hydrogen chloride; H₃PO₂ for hypophosphorous acid; K for potassium; K₂CO₃ for potassium carbonate; KHMDS for potassium bis(trimethylsilyl)amide; Lombardo reagent for dibromomethane-zinc-titanium(IV) chloride; PhLi for phenyl lithium; LDA for lithium diisopropylamide; Li for lithium; LiHMDS for lithium bis(trimethylsilyl)amide; LiOH for lithium hydroxide; MeOH for methanol; MeI for methyl iodide; Mg for magnesium; Na for sodium; NaBH₄ for sodium borohydride; NaBH₃CN for sodium cyanoborohydride; NaHMDS for sodium bis(trimethylsilyl)amide; NaCl for sodium chloride; NaClO for sodium hypochlorite; NaH for sodium hydride; NaHCO₃ for sodium bicarbonate or sodium hydrogen carbonate; Na₂CO₃ sodium carbonate; NaOH for sodium hydroxide; NaOMe for sodium methoxide; Na₂SO₄ for sodium sulfate; NaHSO₃ for sodium bisulfite or sodium hydrogen sulfite; Na₂S₂O₃ for sodium thiosulfate; NH₄HCO₃ for ammonium bicarbonate; NH₄Cl for ammonium chloride; NMO for N-methylmorpholine N-oxide; NaIO₄ for sodium periodate; o/n for overnight; OH for hydroxyl; OsO₄ for osmium tetroxide; Pd for palladium; PDC for pyridinium dichromate; i-PrOAc for isopropyl acetate; Ph for phenyl; PMB for p-methoxybenzyl; rt for room temperature; Ru for ruthenium; SEM for (trimethylsilyl)ethoxymethyl; TBAF for tetrabutylammonium fluoride; TBS for tert-butyl dimethylsilyl; TEA or Et₃N for triethylamine; Tebbe reagent for bis(cyclopentadienyl)-μ-chloro(dimethylaluminum)-μ-methylenetitanium; TEMPO for 2,2,6,6-tetramethyl-1-piperidinyloxy, free radical; Teoc for 2-trimethylsilyl-ethoxycarbonyl; TFA or CF₃COOH for trifluoroacetic acid; THF for tetrahydrofuran; Ti for titanium; TMEDA for N,N,N',N'-tetramethylethylenediamine; TPP or PPh₃ for triphenylphosphine; Ts for tosyl or —SO₂—C₆H₄CH₃; TsOH for p-tolylsulfonic acid; TMS for trimethylsilyl; TMSCl for trimethylsilyl chloride; TTMSS or (Me₃Si)₃SiH for tris(trimethylsilyl)silane; V-50 for 2,2'-azobis(2-methylpropion-amidine)dihydrochloride; VA-44 for 2,2'-azobis[2-(2-imidazolin-2-yl)propane]dihydro-chloride; Zhan-1b catalyst for 1,3-bis(2,4,6-trimethylphenyl)-4,5-dihydroimidazol-2-ylidene[2-(iso-propoxy)-5-(N,N-dimethylaminosulfonyl)phenyl]methylene ruthenium(II) dichloride; or Zn for zinc.

All other abbreviations used herein, which are not specifically delineated above, shall be accorded the meaning which one of ordinary skill in the art would attach.

Synthetic Schemes

The present invention will be better understood in connection with Schemes 1-2, wherein R, PG and X are as previously defined unless otherwise indicated. It will be readily apparent to one of ordinary skill in the art that the process of the present invention can be practiced by substitution of the appropriate reactants and that the order of the steps themselves can be varied.

A general chemical route to the synthesis of the 4-spirocyclopropyl proline and its derivatives (I) is summarized in Scheme 1. The synthesis starts from 4-hydroxyproline or its derivatives (II) which may be oxidized to ketone (III) under conditions known to those skilled in the art. The oxidation can optionally be performed on the carboxylic acid or its corresponding ester. Ketone (III) is then transformed to olefin (IV) by Wittig reaction or using another olefination reagent such as Tebbe reagent or Lombardo reagent. Olefin (IV) is then converted to dihalogenated cyclopropane (V) by reaction with a dihalocarbene, preferably generated via thermal decomposition of a trihaloacetate salt, optionally in the presence of a halide salt or phase-transfer catalyst, as is known to those skilled in the art. The hydrodehalogenation of the dihalogenated cyclopropane (V) to the title cyclopropane (I) can be carried out under reductive radical conditions or single electron transfer conditions.

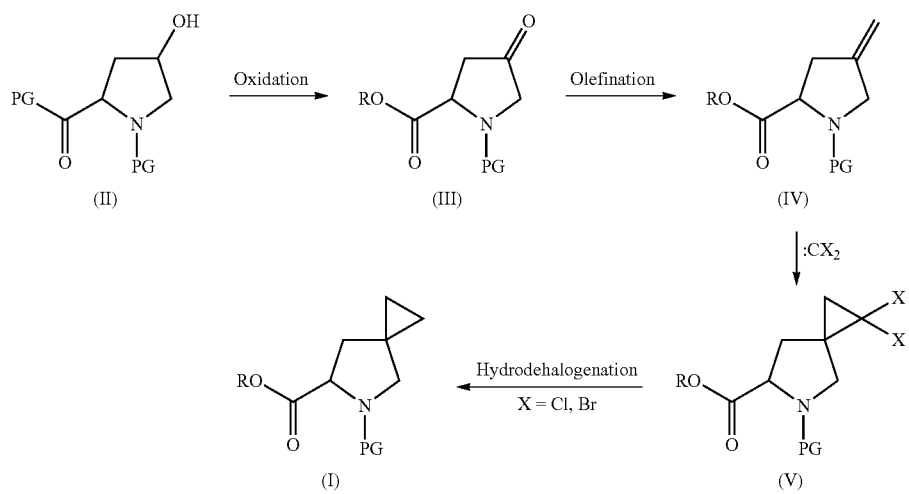

Scheme 1

A representative detailed synthesis of compounds of Formula (I) is illustrated in Scheme 2, wherein PG is as previously defined; preferably, PG is Boc or Cbz.

Scheme 2

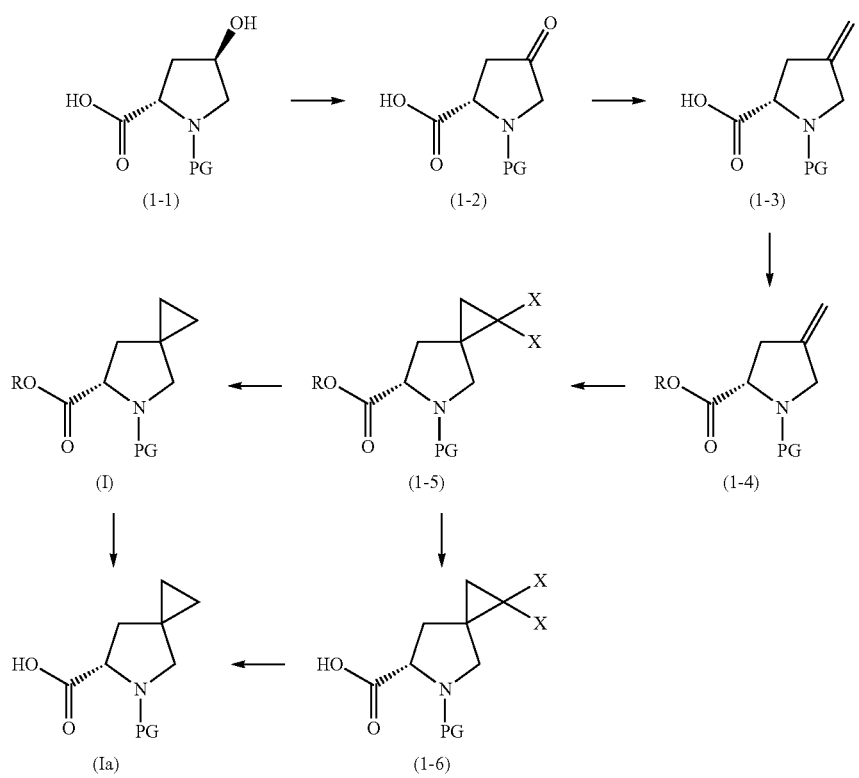

Compounds of Formula (1-2) may be synthesized by reacting compounds of Formula (1-1) (which are either commercially available or may be synthesized by methods known to those skilled in the art) with an oxidizing reagent, such as TEMPO/NaClO, PDC, Dess-Martin periodinane, and that used in Swern oxidation or Corey-Kim oxidation. A comprehensive list of oxidizing reagents and conditions may be found in *Comprehensive Organic Transformations* (R. C. Larock, 2nd ed. page 1234-1249). The reaction typically takes place in an aprotic solvent. The exact reaction conditions and times will vary depending on many factors, such as the structure of the starting material, the choice of the oxidizing reagents, the stoichiometry of the reagents from excess to catalytical amount, and will be known to those skilled in the art. The oxidizing reagents are preferably TEMPO/NaClO.

Compounds of Formula (1-2) may be converted to compounds of Formula (1-3) by olefination through a Wittig reaction or related reactions, in the presence of a strong base. The typical Wittig reagents or related reagents may include $Ph_3PCH_3Br$, $Ph_3PCH_3I$, $(EtO)_2P(O)CH_3$, $Me_3SiCH_2Cl$, or their corresponding polymer-supported forms. Examples of the base may include potassium t-butoxide, lithium t-butoxide, sodium methoxide, sodium ethoxide, LDA, LiHMDS, NaHMDS, and KHMDS. The typical reaction temperature is between −78° C. to 100° C. and the typical duration of the reaction is 1 to 48 hours.

Alternatively, compounds of Formula (1-2) may be treated with a metallated carbene reagent, such as Tebbe reagent or Lombardo reagent to provide compounds of Formula (1-3).

Compounds of Formula (1-4) may be prepared by reacting compounds of Formula (1-3) with an alkylating reagents in the presence of a base. Examples of the bases include, but not limited to, potassium carbonate, sodium bicarbonate, sodium hydroxide, triethylamine, diisopropylethylamine, hexamethyldisilane, and DBU.

Alternatively, compounds of Formula (1-4) may prepared by reacting compounds of Formula (1-3) with an alcohol in the presence of a condensation reagent or water scavenger such as DCC, EDC or the like, optionally in the presence of a base.

Yet alternatively, compounds of Formula (1-3) may be converted to compounds of Formula (1-4) in two steps: 1) mixed anhydride formation between compounds of Formula (1-3) with an acid chloride such as 2,4,6-trichlorobenzoyl chloride, or the like, or a chloroformate such as methyl chloroformate, isobutyl chloroformate, or the like, in the presence of a base such as TEA, DIPEA, DMAP, N-methylmorpholine, or the like; 2) treating the mixed anhydride with an alcohol to afford compounds of Formula (1-3).

Yet alternatively, compounds of Formula (1-4) may be synthesized by direct treatment of compounds of Formula (1-3) with esterification reagents such as diazomethane, (trimethylsilyl)diazomethane.

Compounds of Formula (1-4) may be converted to compounds of Formula (1-5) by reacting with a monohalocarbene or a dihalocarbene, which may be generated by treating dichloromethane, dibromomethane, chloroform or bromoform with a base, optionally in the presence of a phase-transfer catalyst. The base is typically NaOH, KOH, t-BuOK, or the like. Examples of phase-transfer catalyst may include, but not limited to, $Bu_4NCl$, $Bu_4NBr$, $Bu_4NI$, $Et_3BnNBr$, and crown ethers.

Alternatively, compounds of Formula (1-5) may be prepared by reacting compounds of Formula (1-4) with a dihalocarbene generated through the thermal decomposition of a trihaloacetate salt, such as $Cl_3CCO_2Na$, $Br_3CCO_2Na$, optionally in the presence of a halide salt or a phase-transfer catalyst; preferably the halide salt may be also a phase-transfer catalyst. The reaction temperature is typically between 20-200° C. and the reaction time is typically between 1 to 48 hours. Examples of phase-transfer catalysts include Bu$_4$NCl, Bu$_4$NBr, Bu$_4$NI, Et$_3$BnNBr, and crown ethers.

Compounds of Formula (I) may be prepared by reductive hydrodehalogenation of compounds of Formula (1-5) with a low valent metal, preferably in a protic solvent or a combination of protic solvents. Alternatively the reduction may be performed with a low valent metal in the presence of an electron absorbing reagent, such as naphthalene, in a aprotic solvent or a combination of aprotic solvents. Examples of the low valent metal include Zn, Mg, Li, Na, K, and Ti metal. The solvents typically used include but not limited to water, HOAc, MeOH, t-BuOH.

Alternatively, a compound of Formula (1-5) may be converted to a compound of Formula (I) with a reductive radical reagent in the presence of a radical initiator. Representative examples of radical reducing reagents include, but not limited to, stannanes, silanes, low-valent phosphorous and sulfur compounds, such as Bu$_3$SnH, (Me$_3$Si)$_3$SiH, H$_3$PO$_2$, and the like. The initiator is typically AIBN, BPO, or a water-soluble radical initiator such as V-50 or VA-44. The solvents used in the reaction may be protic or aprotic solvents. The reaction is typically conducted at a temperature between 20-200° C. and the reaction time is typically between 1 and 100 hours. In a preferred embodiment of the reaction, the reductive radical reagent is (Me$_3$Si)$_3$SiH or H$_3$PO$_2$.

It should be noted some of the reductive radical reactions described above may be performed catalytically with excess of another reducing reagent. For example, it may be possible to reduce the amount of (Me$_3$Si)$_3$SiH used to a catalytic amount by adding another reducing reagent, such as tetrabutylammonium tetrahydroborate.

Optionally, compounds of Formula (I) where R is not hydrogen may be converted to compounds of Formula (Ia) by removing the R group via deprotective hydrolysis. Representative deprotective hydrolyzing reagents include LiOH (when R=alkyl or aryl), HCl (when R=t-butyl), Zn (when R=—CH$_2$CCl$_3$). Reaction conditions vary depending on the choice of the deprotective hydrolyzing agent and will be known to those skilled in the art, and are described generally in T. H. Greene and P. G. M. Wuts, *Protective Groups in Organic Synthesis,* 3rd edition, John Wiley & Sons, New York (1999).

Alternatively, compounds of Formula (1-5) may be converted to compounds of Formula (Ia) through intermediate (1-6) by switching the order of deprotection and hydrodehalogenation using procedures similar to those described above.

Optionally, compounds of Formula (I) where PG is not hydrogen may be converted to compounds of Formula (Ib) by removing the protective PG group. Reaction conditions vary depending on the identity of PG and the choice of the deprotecting reagent and will be known to those skilled in the art, and are described generally in T. H. Greene and P. G. M. Wuts, *Protective Groups in Organic Synthesis,* 3rd edition, John Wiley & Sons, New York (1999).

Optionally, compounds of Formula (I) where neither R nor PG is hydrogen may be converted to compounds of Formula (Ic) by removing the R group via hydrolysis and by removing the PG group as described above. The R and PG groups can be removed in either order, or, in certain embodiments, they can be removed simultaneously.

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

Example 1

Preparation of (S)-1-(tert-butoxycarbonyl)-4-oxopyrrolidine-2-carboxylic acid

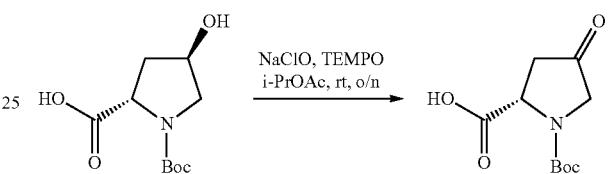

To a solution of (2R,4S)-1-(tert-butoxycarbonyl)-4-hydroxypyrrolidine-2-carboxylic acid (92 g, 0.398 mol) in isopropyl acetate (460 mL) was added TEMPO (2.49 g, 0.05 eq) at 0° C. A solution of NaClO (12.5 wt %, 370 mL) was added dropwise to the reaction mixture while maintaining the temperature at 0-5° C. The reaction was slowly allowed to warm to room temperature and stirred at room temperature overnight. The organic layer was separated and the aqueous layer was treated with 1M KHSO$_4$ solution and extracted with isopropyl acetate (2×150 mL). The combined organic layers were washed with 5% Na$_2$S$_2$O$_3$ (100 mL), brine, dried (Na$_2$SO$_4$), filtered and evaporated to provide the title compound as a solid. It was triturated with acetonitrile (40 mL), filtered and dried to give a white solid (52.3 g). The filtrate was concentrated, treated with 50% ethyl acetate in hexanes (20 mL) and stored in refrigerator for overnight before being filtered and dried to give a white solid (3.94 g). Totally obtained 56.24 g (62%). $^1$H NMR (500 MHz, DMSO-d$_6$): 12.99 (br s, 1H), 4.54-4.50 (m, 1H), 3.84-3.77 (m, 1H), 3.68-3.63 (m, 1H), 3.15-3.06 (m, 1H), ~2.49 (m, 1H, overlapped with DMSO), 1.40 and 1.37 (2 s, 9H).

Example 2

Preparation of (S)-1-(tert-butoxycarbonyl)-4-methylenepyrrolidine-2-carboxylic acid

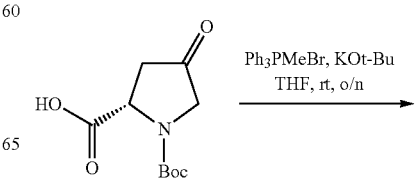

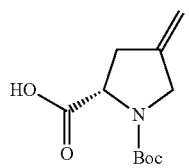

To a mixture of methyltriphenylphosphonium bromide (236.4 g, 2.7 eq) in THF (1 L) was rapidly added potassium tert-butoxide (75.6 g, 2.75 eq) while maintaining the temperature around 0° C. The reaction mixture was allowed to warm to room temperature and stirred at room temperature for 2 hours, and re-cooled to 0° C. (S)-1-(tert-butoxycarbonyl)-4-oxopyrrolidine-2-carboxylic acid (56.2 g, 0.245 mol) was added portionwise to the reaction mixture while maintaining the temperature below 5° C. Then, the reaction was allowed to warm to room temperature and stirred at room temperature overnight before being re-cooled to 0° C. and quenched by addition of saturated $NaHCO_3$ solution (500 mL) and water (200 mL). The mixture was evaporated. The aqueous layer was extracted with tert-butyl methyl ether (2×400 mL). The aqueous layer was filtered through a pad of celite and the filtrate was acidified with 6N HCl (200 mL) and extracted with ethyl acetate (2×1 L). The combined organic layers were washed with brine, dried ($Na_2SO_4$), filtered and evaporated to dryness. The residue was dissolved in ethyl acetate (0.7 L), extracted with 0.5 N NaOH (0.7 and 0.3 L). The aqueous layer was acidified with 6N HCl (100 mL), extracted with ethyl acetate (1 L and 0.8 L). The combined organic layers were washed with brine, dried ($Na_2SO_4$), filtered and evaporated to dryness. The residue was dissolved in 50% ethyl acetate in cyclohexane (150 mL), slowly evaporated to give a yellowish solid. It was filtered and dried to give the title compound (26 g). The filtrate was evaporated to give a yellowish solid, filtered and dried to provide the title compound (10 g). Total 36 g (65%) as a white solid. Also, the residue contained 18 g of the product as 80% purity. $^1$H NMR (500 MHz, $CDCl_3$): 5.04-5.02 (m, 2H), 4.53 (dd, J=8.4, 3.2 Hz, 0.5H), 4.42 (d, J=9.3 Hz, 0.5H), 4.09-3.98 (m, 2H), 3.05-2.69 (m, 2H), 1.49 and 1.43 (2 s, 9H).

Example 3

Preparation of (S)-1-tert-butyl 2-methyl 4-methylenepyrrolidine-1,2-dicarboxylate

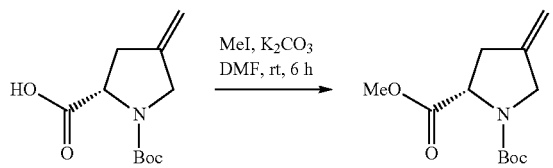

To a mixture of (S)-1-(tert-butoxycarbonyl)-4-methylenepyrrolidine-2-carboxylic acid (35 g, 154 mol) in DMF (155 mL) was added potassium carbonate (32 g, 1.5 eq) at room temperature. The mixture was stirred at room temperature for 1 hr before being cooled with a water bath. Methyl iodide (19.2 mL, 2 eq) was added dropwised. The mixture was stirred at room temperature for 6 hr. The reaction mixture was filtered through a pad of celite, diluted with ethyl acetate (300 mL), washed with water (200 mL). The aqueous layer was extracted with ethyl acetate (300 and 200 mL). The combined organic layers were washed with 10% $Na_2S_2O_3$ solution (100 mL), water (3×200 mL) and brine, dried ($Na_2SO_4$), filtered and evaporated to dryness. The residue was passed through a silica gel (2 wt. volumes) pad with 0-15% ethyl acetate in hexanes to afford the title compound (37.06 g, quantitative yield) as a colorless oil. $^1$H NMR (500 MHz, $CDCl_3$): 5.03 and 4.99 (2 br s, 2H), 4.51 (dd, J=9.5, 2.7 Hz) and 4.40 (dd, J=9.5, 3.3 Hz, 1H), 4.09 and 4.06 (2 br s, 2H), 3.73 (s, 3H), 3.01-2.92 (m, 1H), 2.65-2.60 (m, 1H), 1.47 and 1.42 (2 s, 9H).

Example 4

Preparation of Sodium Tribromoacetate

To a mixture of tribromoacetic acid (131 g, 0.44 mol) and phenolphthalein (220 mg) in abs. MeOH (400 mL) was dropwise added 25% MeONa in MeOH until the pink color would not disappear. 100 mL of MeONa solution was consumed. The reaction mixture was evaporated off while keeping the bath temperature below 20° C. and co-evaporated with 1,2-dichloroethane (3×100 mL). The residue was dried on the vacuum pump to give the title compound (139 g) as a light pink solid.

Example 5

Preparation of (6S)-5-tert-butyl 6-methyl 1,1-dibromo-5-azaspiro[2.4]heptane-5,6-dicarboxylate

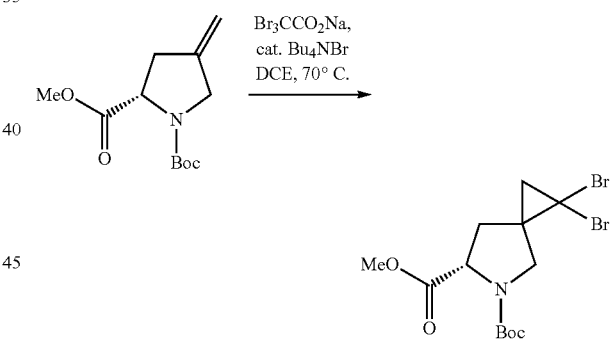

To a mixture of (S)-1-tert-butyl 2-methyl 4-methylenepyrrolidine-1,2-dicarboxylate (6 g, 24.9 mmol) and tetrabutylammonium bromide (161 mg, 0.02 eq) in anhydrous 1,2-dichloroethane (60 mL, 10 volumes) was added sodium tribromoacetate (17.48 g, 2.2 eq). The mixture was degassed and filled with $N_2$ gas. It was heated at 70° C. for 2.5 hrs before additional sodium tribromoacetate (2.4 g, 0.3 eq) was added. The mixture was heated at 70° C. for 40 min. After the completion of the reaction, it was allowed to cool to room temperature and evaporated. The residue was diluted with 30% hexanes in tert-butyl methyl ether (100 mL) and filtered through a pad of celite. The filtrate was washed with water and brine, dried ($Na_2SO_4$), filtered and evaporated to dryness. The residue was passed through a silica gel (5.5 wt. volumes) pad with 0-15% tert-butyl methyl ether in hexanes and concentrated to afford the title compound (9.09 g, 88%) as a yellow oil as a mixture of two regioisomers. $^1$H NMR (500 MHz, $CDCl_3$): 4.63-4.44 (m, 1H), 3.92-3.86 (m, 1H), 3.79 and 3.74 (2 s, 3H), 3.53-3.42 (m, 1H), 2.83-2.35 (m, 1.5H), 1.91-1.70 (m, 2.5H), 1.48 and 1.43 (2 s, 9H). ESI MS m/z (M+H)+ 413.85.

Example 6

Preparation of (6S)-1,1-dibromo-5-(tert-butoxycarbonyl)-5-azaspiro[2.4]heptane-6-carboxylic acid

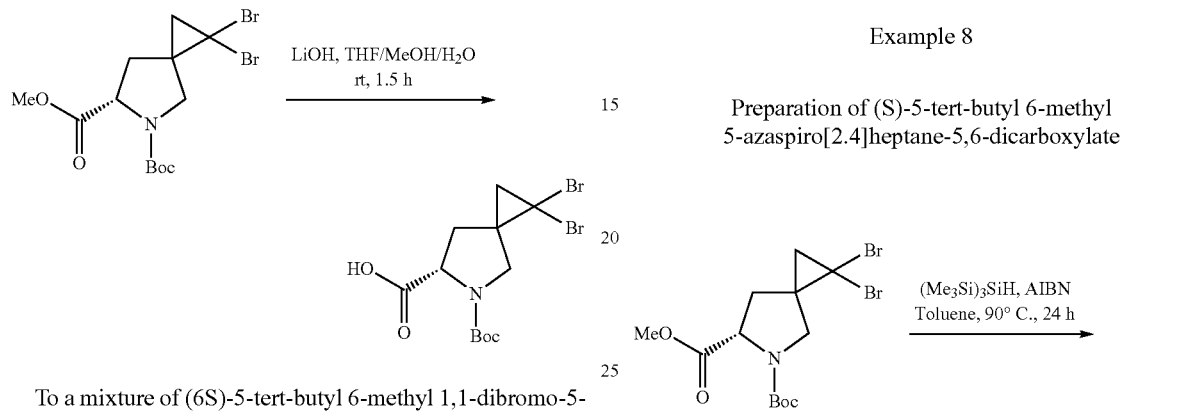

To a mixture of (6S)-5-tert-butyl 6-methyl 1,1-dibromo-5-azaspiro[2.4]heptane-5,6-dicarboxylate (3.05 g, 7.39 mmol) in THF-MeOH-water (35 mL, 14 mL and 14 mL respectively) was added LiOH monohydrate (930 mg, 3 eq). The mixture was stirred at room temperature for 1.5 hr before being evaporated off. The aqueous residue was acidified with 1M HCl, extracted with dichloromethane (2×50 mL). The combined organic layers were washed with water and brine, dried (Na$_2$SO$_4$), filtered and evaporated to give the title compound (quantitative yield) as a light yellow solid. $^1$H NMR (500 MHz, CDCl$_3$): 10.45 (br s, 1H), 4.65-4.45 (m, 1H), 3.99-3.86 (m, 1H), 3.53-3.31 (m, 1H), 2.87-1.95 (m, 2H), 1.86-1.73 (m, 2H), 1.49, 1.48 and 1.44 (3 s, 9H).

Example 7

Preparation of (S)-5-(tert-butoxycarbonyl)-5-azaspiro[2.4]heptane-6-carboxylic acid

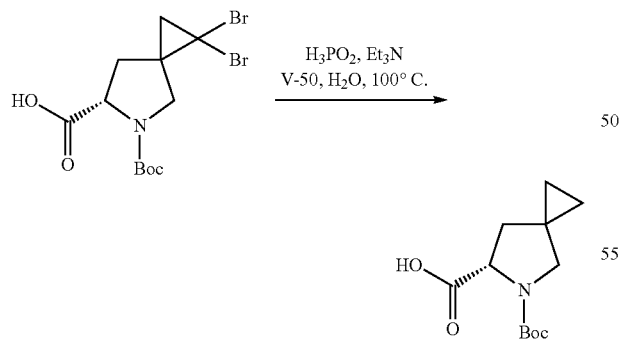

To a mixture of (6S)-1,1-dibromo-5-(tert-butoxycarbonyl)-5-azaspiro[2.4]heptane-6-carboxylic acid (8.7 g, 21.8 mmol), 50 wt % hypophosphorus acid (25.9 mL, 9 eq) and triethylamine (44.3 mL, 10 eq) in water (104 mL, 12 volumes) was added V-50 (591 mg, 0.1 eq) in 2 mL of 50% aqueous acetonitrile. The mixture was heated at 100° C. During the heating, additional 0.1 eq of V-50 was added to the reaction mixture every 30 minutes. Totally, 0.7 eq of V-50 was added.

After heating at 100° C. for 4 hrs, the reaction mixture was evaporated and treated with 2N NaOH. It was extracted with ethyl acetate (2×50 mL). The aqueous layer was acidified with 2N HCl, extracted with ethyl acetate (2×50 mL). The combined organic layers were washed with water and brine, dried (Na$_2$SO$_4$), filtered and evaporated to give the title compound (3.63 g, 69%) as a light yellow solid. $^1$H NMR (500 MHz, CDCl$_3$): 4.51-4.42 (m, 1H), 3.48-3.11 (m, 2H), 2.27-1.93 (m, 2H), 1.50/1.45 (two overlapping s, 9H), 0.71-0.59 (m, 4H).

Example 8

Preparation of (S)-5-tert-butyl 6-methyl 5-azaspiro[2.4]heptane-5,6-dicarboxylate

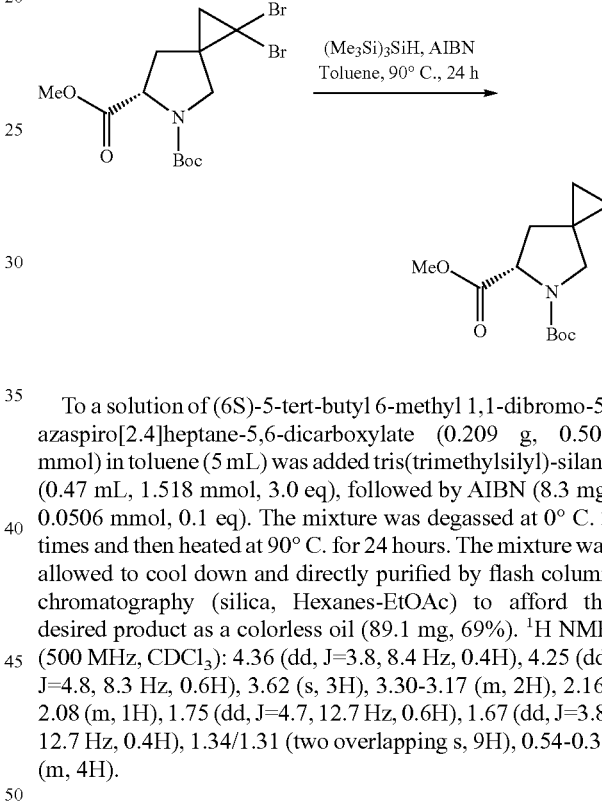

To a solution of (6S)-5-tert-butyl 6-methyl 1,1-dibromo-5-azaspiro[2.4]heptane-5,6-dicarboxylate (0.209 g, 0.506 mmol) in toluene (5 mL) was added tris(trimethylsilyl)-silane (0.47 mL, 1.518 mmol, 3.0 eq), followed by AIBN (8.3 mg, 0.0506 mmol, 0.1 eq). The mixture was degassed at 0° C. 3 times and then heated at 90° C. for 24 hours. The mixture was allowed to cool down and directly purified by flash column chromatography (silica, Hexanes-EtOAc) to afford the desired product as a colorless oil (89.1 mg, 69%). $^1$H NMR (500 MHz, CDCl$_3$): 4.36 (dd, J=3.8, 8.4 Hz, 0.4H), 4.25 (dd, J=4.8, 8.3 Hz, 0.6H), 3.62 (s, 3H), 3.30-3.17 (m, 2H), 2.16-2.08 (m, 1H), 1.75 (dd, J=4.7, 12.7 Hz, 0.6H), 1.67 (dd, J=3.8, 12.7 Hz, 0.4H), 1.34/1.31 (two overlapping s, 9H), 0.54-0.39 (m, 4H).

Example 9

Preparation of (S)-5-(tert-butoxycarbonyl)-5-azaspiro[2.4]heptane-6-carboxylic acid

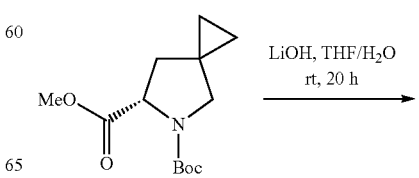

-continued

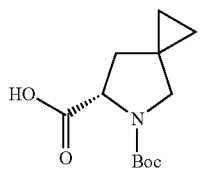

To a solution of (S)-5-tert-butyl 6-methyl 5-azaspiro[2.4]heptane-5,6-dicarboxylate (0.436 g, 1.708 mmol) in ethanol (4 mL) was added a solution of LiOH.H$_2$O (86.0 mg, 2.049 mmol, 1.2 eq) in H$_2$O (2 mL) at room temperature. The mixture was stirred at room temperature for 20 hours. EtOH was removed by rotavapor. The aqueous residue was diluted with H$_2$O and extracted with Et$_2$O. The aqueous layer was cooled with an ice bath and acidified to pH ~2 with 1 N HCl. The resulting milky solution was extracted with a mixed solvent of EtOAc and CH$_2$Cl$_2$. The organic layer was dried (Na$_2$SO$_4$), filtered and evaporated. The residue was dried under vacuum to afford the desired product as an off-white solid (0.422 g, 100%).

Example 10

Preparation of (S)-5-(tert-butoxycarbonyl)-5-azaspiro[2.4]heptane-6-carboxylic acid

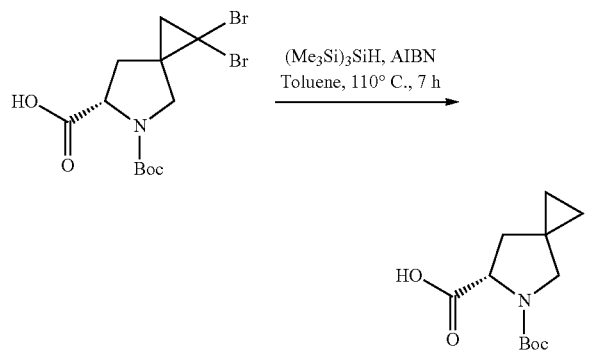

To a degassed solution of (6S)-1,1-dibromo-5-(tert-butoxycarbonyl)-5-azaspiro[2.4]heptane-6-carboxylic acid (580 mg, 1.45 mmol) in toluene (6 mL) was added the tris(trimethylsilyl)silane (1.35 mL, 4.36 mmol, 3.0 eq) and AIBN (24 mg, 0.145 mmol, 0.1 eq). The solution was heated at 110° C. for 3 hours. Another batch of tris(trimethylsilyl)silane (0.45 mL 1.45 mmol, 1.0 eq) and AIBN (10 mg) was added. The solution was heated at 110° C. for 2 more hours. A third batch of tris(trimethylsilyl)silane (0.45 mL 1.45 mmol, 1.0 eq) and AIBN (10 mg) was added. The solution was heated at 110° C. for 2 more hours. After being allowed to cool down, the solution was diluted with EtOAc (5 mL). This organic phase was extracted with aqueous K$_2$CO$_3$ (1 M, 10 mL×3). The combined aqueous extractions were cooled (ice/water) and acidified to pH 2 with concentrated HCl. This acidified aqueous phase was extracted with EtOAc (×3), dried (Na$_2$SO$_4$), filtered and evaporated. The residue was dried under vacuum to afford the desired compound as colorless oil (135 mg, 39%).

Example 11

Preparation of (S)-5-tert-butyl 6-methyl 5-azaspiro[2.4]heptane-5,6-dicarboxylate

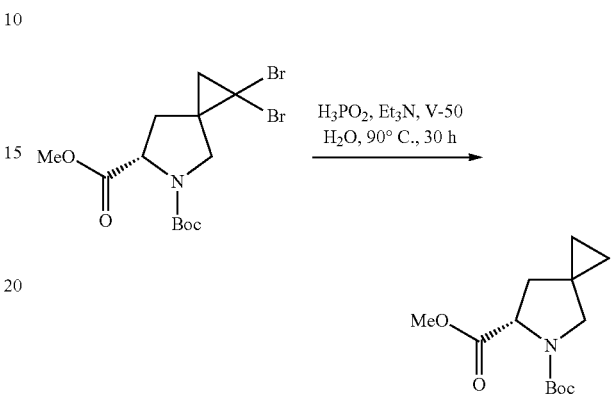

To the solution of (6S)-5-tert-butyl 6-methyl 1,1-dibromo-5-azaspiro[2.4]heptane-5,6-dicarboxylate (69 mg, 0.167 mmol) in water (1 mL) and ACN (0.5 mL) were added the hypophosphorous acid (0.078 mL, 0.96 mmol), TEA (0.27 mL, 1.92 mmol) and V-50 (4.5 mg, 0.0167 mmol). The solution was degassed and was heated at 90° C. for 15 hours. After being cooled, the solution was diluted with H$_2$O, extracted with EtOAc (×3) and was dried (Na$_2$SO$_4$), concentrated. The crude product was treated under the conditions above for another 15 hours. After cooled, the solution was diluted with H$_2$O (10 mL) and tuned to pH 4 by adding aq HCl (4 N). The aqueous phase was extracted with EtOAc (×3), dried (Na$_2$SO$_4$). After concentrated under vacuum, the title compound was obtained as colorless oil (20 mg, 42%).

While this invention has been particularly shown and described with references to preferred embodiments thereof, it will be understood by those skilled in the art that various changes in form and details may be made therein without departing from the scope of the invention encompassed by the appended claims.

What is claimed is:
1. A process for the preparation of a compound of Formula (I):

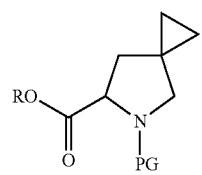

wherein R is selected from the group consisting of hydrogen, C$_1$-C$_8$ alkyl, C$_2$-C$_8$ alkenyl, C$_2$-C$_8$ alkynyl, C$_3$-C$_8$ cycloalkyl, C$_3$-C$_8$ cycloalkenyl, heterocyclic, aryl, and heteroaryl, each optionally substituted; and PG is selected from the group consisting of —R, —C(O)—R, —C(O)—OR, —S(O)$_2$—R, —C(O)NR$_2$, and —S(O)$_2$NR$_2$;

said process comprising:

(a) reacting a compound of Formula (II):

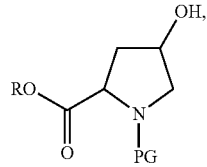

with an oxidizing reagent to yield a compound of Formula (III):

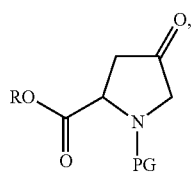

(b) reacting the compound of Formula (III) with an olefination reagent to provide a compound of Formula (IV):

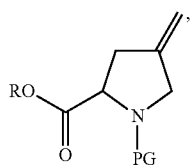

(c) reacting the compound of Formula (IV) with a monohalocarbene or dihalocarbene, wherein each halo is independently bromo or chloro, to yield a compound of Formula (V):

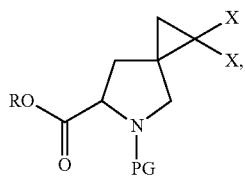

wherein X at each occurrence is independently selected from the group consisting of hydrogen, bromine and chlorine wherein at least one of the two X groups is chlorine or bromine;

(d) maintaining the compound of Formula (V) under conditions for reductive hydrodehalogenation to provide a compound of Formula (I):

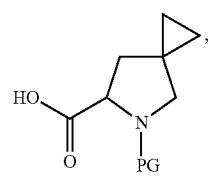

wherein R and PG are as previously defined; and (e) optionally,
  (i) when R is not hydrogen, hydrolyzing the compound of Formula (I) to yield a compound of Formula (Ia):

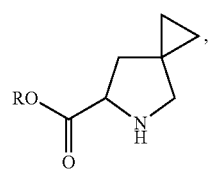

(ii) when PG is not hydrogen, deprotecting the compound of Formula I to yield a compound of Formula (Ib):

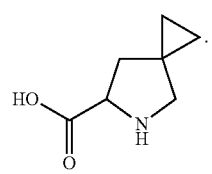

or (iii) when neither R nor PG is hydrogen, hydrolyzing and deprotecting the compound of Formula I to yield the compound of Formula (Ic),

2. The process of claim 1, wherein the dihalocarbene of step (c) is generated by
   thermal decomposition of a trihaloacetate salt, optionally in the presence of a halide salt or a phase-transfer catalyst; and
   the conditions for reductive hydrodehalogenation of step (d) comprise reductive radical conditions or single electron transfer conditions.

3. The process of claim 1, wherein R is hydrogen, optionally substituted alkyl or optionally substituted aryl.

4. The process of claim 1, wherein PG is —C(O)—OR.

5. The process of claim 1, wherein R is hydrogen, methyl, benzyl, tert-butyl or phenyl; PG is hydrogen, Boc or Cbz; and X at each occurrence is independently hydrogen or bromine and at least one of the two X groups is bromine.

6. The process of claim 1, wherein step (c) comprises dihalocarbene cyclization of the exocyclic olefinic double bond of the compound of Formula (IV) to give the dihalogenated cyclopropane roup of the compound of Formula (V), and step (d) comprises reductive hydrodehalogenation of the compound of Formula (V).

7. The process of claim 1, wherein the dihalocarbene is generated by thermal decomposition of a trihaloacetate salt, optionally in the presence of a halide or phase-transfer catalyst.

8. The process of claim 1, wherein the dihalocarbene is generated by thermal decomposition of sodium trichloroacetate or sodium tribromoacetate in the presence of a quaternary ammonium bromide salt or a quaternary ammonium chloride salt.

9. The process of claim 1, wherein step (d) comprises reacting the compound of Formula (V) with a reductive radical reagent or a single-electron reagent.

10. The process of claim 9, wherein the reductive radical reagent is a stannane, a silane, a sulfide, or a low-valent phosphorous reagent, in the presence of a radical initiator.

11. The process of claim 10, wherein the reductive radical reagent is tris(trimethylsilyl)silane or hypophosphorous acid ($H_3PO_2$).

\* \* \* \* \*